United States Patent [19]

King

[11] 4,426,541

[45] Jan. 17, 1984

[54] PROCESS FOR PRODUCTION OF ALIPHATIC ALCOHOLS

[75] Inventor: Terry S. King, Baton Rouge, La.

[73] Assignee: Exxon Research & Engineering Co., Florham Park, N.J.

[21] Appl. No.: 358,644

[22] Filed: Mar. 16, 1982

[51] Int. Cl.$^3$ ............................................. C07C 29/14
[52] U.S. Cl. .................................. 568/881; 568/882; 568/883
[58] Field of Search ..................... 568/881, 882, 883

[56] References Cited

U.S. PATENT DOCUMENTS

| | | | |
|---|---|---|---|
| 2,595,096 | 4/1952 | Parker | 260/638 |
| 2,709,714 | 5/1955 | Mertzweiller | 568/883 |
| 2,760,994 | 8/1956 | Gwynn | 568/881 |
| 2,771,493 | 11/1956 | Jacks et al. | 568/881 |
| 2,815,390 | 12/1957 | Gwynn et al. | 568/882 |
| 3,491,158 | 1/1970 | Reich | 568/881 |
| 3,880,940 | 4/1975 | Baer et al. | 260/639 |
| 4,182,721 | 1/1980 | DeThomas et al. | 260/347 |

FOREIGN PATENT DOCUMENTS 1219038  1/1971  United Kingdom ................ 568/881

OTHER PUBLICATIONS

S. A. Bartkiewicz/L. C. Kenyon, "Automated Determination of Trace Carbonyls", *Analytical Chemistry*, vol. 35., No. 3, pp. 1122–1123 (Mar. 1963).

O. Weissler et al., *Sulfide Catalysts, Their Properties and Applications*, 171–173, Pergamon press, (1973).
R. J. Morrison/ R. N. Boyd, "Organic Chemistry", p. 636, 2nd Edition (1966).
German Offenlegungschrift, Patent 1,929,920, Chem. Abs. vol. 74, 76007f.
Japan, Patent 74/06290, Chem. Abs. vol. 82, 86084h.
U.S.S.R., Patent 225,155, Chem. Abs. vol. 70, 19570c.
East Germany, Patent 106,347, Chem. Abs. vol. 81, 151525y.
Germany, Patent 1,203,235, Chem. Abs, vol. 64, 12548G.
Germany, Patent 1,276,618, Chem. Abs. vol. 70, 37167f.
U.S.S.R., Patent 277,761, Chem. Abs. vol. 74, 41896t.

*Primary Examiner*—J. E. Evans
*Attorney, Agent, or Firm*—Jack B. Murray, Jr.

[57] ABSTRACT

Aliphatic alcohols are produced by an improved hydrogenation of the corresponding saturated aliphatic aldehydes in the presence of organo-sulfur impurities by partially hydrogenating the aldehydes in a first hydrogenation zone in the presence of a sulfided hydrogenation catalyst at a temperature within the range of from about 180° to 260° C., followed by completion of the hydrogenation in the second hydrogenation zone in the presence of a metallic nickelcontaining hydrogenation catalyst. The second hydrogenation zone employs a lower temperature than is used in the first and is selected within the range of from about 175° to 250° C.

8 Claims, No Drawings

PROCESS FOR PRODUCTION OF ALIPHATIC ALCOHOLS

BACKGROUND OF THE INVENTION

1. Field of the Invention

This invention relates generally to the production of aliphatic alcohols and, in particular, the hydrogenation of oxo aldehydes to the corresponding aliphatic alcohols.

2. Description of the Prior Art

In the well-known oxo process, olefins are hydroformylated by reaction with carbon monoxide and hydrogen, generally charged as syn gas mixtures, in the presence of a cobalt or other oxo catalyst to form a mixture of the corresponding oxo aldehydes and alcohols. Thereafter, the product mixture is recovered and the oxo catalysts are removed by known means to provide a demetalled crude oxo mixture containing the aldehydes and alcohols. This mixture is then generally hydrogenated to convert the aldehydes to additional quantities of the alcohol. The alcohols are then recovered by various means and are widely used as chemical intermediates in the manufacture of plasticizers, detergents, solvents and the like.

U.S. Pat. No. 2,595,096 discloses that the hydrogenator may contain a mass of any conventional hydrogenation catalyst, for example, nickel, copper chromite, sulfactive hydrogenation catalysts such as tungsten sulfide, nickel sulfide, molybdenum sulfide and the like.

In U.S.S.R. Pat. No. 225,155 (as abstracted at Vol. 70 Chem. Abs. 19570c) aliphatic alcohols are prepared by hydrogenation of oxo aldehydes containing sulfur compounds in a first hydrogenation stage using a zinc-chromium catalyst, followed by a second stage hydrogenation in the presence of a nickel-chromium catalyst. Other similar two-stage hydrogenations are disclosed in U.S.S.R. Pat. No. 277,761, as abstracted in Vol. 74, Chem. Abs. 41896t (copper/nickel-chromium); German Offenlegungschrift No. 1,929,920, as abstracted in Vol. 74 Chem. Abs. 76007f, (copper/nickel-chromium); German Pat. No. 1,276,618, as abstracted at Vol. 70 Chem. Abs. 37167f (copper and nickel/nickel or palladium); British Pat. No. 1,219,038 (copper/nickel-chromium); and Japanese Pat. No. 74/06290, as abstracted at Vol. 82 Chem. Abs. 86084h (Raney nickel/palladium).

U.S. Pat. No. 4,182,721 discloses catalysts comprising Raney nickel containing absorbed molybdenum. Other nickel-molybdenum hydrogenation catalysts are disclosed in German Pat. No. 1,203,235 (as abstracted in Vol. 64 Chem. Abs. 12548G); East German Pat. No. 106,347 (as abstracted in Vol. 81 Chem. Abs 151525y); and U.S. Pat. No. 3,880,940. Other prior art sulfided aldehyde hydrogenation catalysts are discussed in O. Weisser, et al., *Sulfide Catalysts, Their Properties and Applications*, 171-173 (Pergamon Press 1973).

SUMMARY OF THE INVENTION

An improved process for hydrogenating oxo aldehydes to the corresponding alcohols in the presence of organo-sulfur impurities is provided in which the oxo aldehydes are first partially hydrogenated in the presence of a sulfided hydrogenation catalyst at a temperature within the range of from about 180° to 260° C., followed by further hydrogenation in the presence of a metallic nickel containing hydrogenation catalyst at a temperature within the range of from about 175° to 250° C. It has been surprisingly found that the second stage, nickel catalyst efficiently absorbs organo-sulfur impurities while continuing to efficiently hydrogenate the aldehyde.

DETAILED DESCRIPTION OF THE INVENTION

According to the present invention, aldehydes are hydrogenated in a series of hydrogenation zones to produce the corresponding alcohols. While not critical to the process of this invention, the process is particularly adapted for hydrogenation of aldehydes produced by the oxo process wherein olefins are hydroformylated in the presence of cobalt catalysts and syn gas to form a crude oxo effluent from which the cobalt catalysts are then removed by any of the means known to the prior art. (A detailed description of the oxo reaction and the catalyst removal step is not believed to be critical to an understanding of the hydrogenation process of this invention.) The demetalled crude oxo effluent which is thereby obtained is preferably substantially free of dissolved cobalt catalysts, and most preferably contains less than about 1 ppm by weight of cobalt catalyst (calculated as elemental Co.).

The amount of aldehydes and alcohols in the feed to the first hydrogenation zone of this invention can vary widely. In the case of a demetalled crude oxo effluent, the aldehydes will be generally present in these feeds in an amount of from about 10 to 90 wt. %, preferably from about 30 to about 60 wt. %, and the alcohols will be present in an amount of from about 1 to 60 wt. %, preferably from about 5 to 20 wt.%.

The aldehydes selected for use in this invention will generally comprise (straight and branched chain) saturated aliphatic aldehydes having from 6 to 20 carbon atoms. Exemplary of such aldehydes, therefore, are caproaldehyde, heptaldehyde, octaldehyde, decaldehyde, dodecaldehyde and $CH_3(CH_2)_{14}CHO$. Accordingly, the alcohols which will be produced will correspond to the aldehyde and will therefore generally comprise (straight and branched chain) saturated aliphatic alcohols having from 6 to 20 carbon atoms per molecule. Exemplary product alcohols are primary normal aliphatic alcohols such as 1-hexanol, 1-heptanol, 1-octanol, 1-nonanol, 1-decanol, 1-undecanol, 1-dodecanol, 1-tridecanol, 1-tetradecanol, 1-pentadecanol, 1-hexadecanol, 1-heptadecanol, 1-octadecanol, 1-nonadecanol, 1-eicosanol, and the like, primary branched aliphatic alcohols such as 2-methyl-1-pentanol, 2-ethyl-1-butanol, 2-ethyl-1-hexanol, 3,5-dimethyl-1-hexanol, 2,2,4-trimethyl-1-pentanol, and the like, secondary aliphatic alcohols such as 4-methyl-2-pentanol, 2-octanol, 2,6-dimethyl-4-heptanol, 2,6,8-trimethyl-4-nonanol, and the like, and highly branched detergent alcohols such as tridecyl alcohol, hexadecyl alcohol, tetradecyl alcohol, heptadecyl alcohol and the like. It will be understood that alcohol mixtures can also be formed. Thus, for example hexylalcohol will generally be a mixture of 1-hexanol, methyl-1-pentanols and 2-ethyl-1-butanol. Similarly, isooctyl alcohol is generally a mixture of 3,4-dimethyl-1-hexanol, 3,5-dimethyl 1-hexanol, 4,5-dimethyl-1-hexanol, methyl-1-heptanols, and other primary alcohols.

The feed to the hydrogenation will generally also contain organo-sulfur compounds which, for example, are formed during the oxo reaction as a result of sulfur contamination in the olefin feed. The quantity and identity of the organo sulfur compounds which can be present in the hydrogenation feed can vary widely and will depend on such factors as the type of aldehyde to be treated, the conditions employed in the oxo reaction, the nature of the sulfur impurities in the feed and other factors. Generally, however, these organo sulfur compounds can be characterized as at least one member selected from the group consisting of sulfides, sulfones and sulfoxides, and more typically at least one member of the compounds having the following formulae: R-S-R',

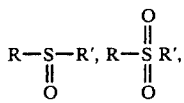

wherein R and R' are the same or different and are alkyl of from 1 8 carbon atoms. Most typically, R and R' in the above formulae are independently the same and are alkyl of from 1 to 4 carbon atoms.

These organo sulfur impurities will be generally present in an amount of from about 5 to 500 ppm, and more usually from about 10 to 50 ppm, calculated as elemental sulfur and based on the total aldehyde feed to the hydrogenation process of this invention.

The aldehyde hydrogenation of this invention is performed in a series of two separate hydrogenation zones. In the first hydrogenation zone the aldehyde-containing feed is contacted with a sulfided hydrogenation catalyst, optionally on a support, at a temperature within the range of from about 180° to 260° C. and preferably from about 220° to 250° C. in the presence of gaseous hydrogen, which is also introduced to the first hydrogenation zone. The $H_2$ partial pressure in the first hydrogenation zone is generally from about 150 to about 220 atmospheres and preferably from about 170 to about 210 atmospheres.

The first stage hydrogenation catalyst comprises a member selected from the group consisting of sulfides of Mo, Ni and W and mixtures thereof. Illustrative of such first stage sulfided catalysts are $MoS_2$, NiS, $NiS_2$, $Ni_3S_2$, $WS_2$, $WS_2.NiS$, $WS_2.2NiS$, $NiS.MoS_2$ and the like. Such sulfided hydrogenation catalysts are known.

Molybdenum sulfide catalysts are preferred.

The molybdenum sulfide catalyst contains molybdenum chemically combined with sulfur, and can be represented as $MoS_x$ wherein "x" is from 1.8 to 2.2. Molybdenum disulfide ($MoS_2$) is most preferred.

The first stage catalyst is preferably supported. The nature of the support is not critical so long as it is thermally stable under the conditions of hydrogenation. Exemplary of suitable thermally stable supports are carbon, kieselguhr, silica and alumina.

The aldehyde feed is generally introduced to the first hydrogenation zone at a liquid hourly space velocity of from about 0.3 to 2.0 v/v/hr., and more preferably from about 0.8 to 1.4 v/v/hr.

In the first hydrogenation zone, generally at least 70 wt.%, more preferably from about 90 to 99 wt.%, of the aldehyde is hydrogenated to the corresponding alcohol. The effluent from the first hydrogenation zone will therefore generally comprise unreacted aldehyde, unreacted hydrogen, alcohol product, and organo-sulfur compound impurities. The concentration of alcohol product, unreacted aldehyde and organo-sulfur compound impurities can vary widely. Representative ranges for such concentrations are: from about 1 to 5 wt.% aldehyde, from about 70 to 90 wt.% alcohol, and from about 10 to 50 ppm organo-sulfur compound impurities, in addition to from about 2 to 20 wt.% of heavy by-products (such as those formed by dimerization and higher oligomerization of either the aldehyde or alcohol). Typically, such heavy by-products are higher boiling than either the product alcohol or the unreacted aldehyde and comprise such classes of compounds as dimer and trimer aldehydes, alcohol, esters, ethers and the like. Thus, for example, in the case of hydrogenation of a mixture of hexaldehyde, heptaldehyde and octaldehyde, these heavy by-products comprise such compounds as $C_{12}$, $C_{14}$ and $C_{16}$ ethers and esters, in addition to heavy unknowns. The effluent from the first hydrogenation zone will also generally be characterized by a carbonyl number of about 1 mg KOH/gram of sample.

The effluent from the first hydrogenation zone (optionally after being degassed to remove the excess hydrogen) is passed to the second hydrogenation reaction zone wherein it is contacted with a nickel hydrogenation catalyst at a temperature in the range of from about 175° to 250° C., and preferably from about 200° to about 240° C., and at a $H_2$ pressure of from about 100 to about 210 atmospheres, preferably from about 180 to 200 atmospheres. Gaseous hydrogen is introduced to the second hydrogenation zone either with the partially hydrogenated aldehyde feed or via a separate conduit (or both), and additional quantities of the aldehydes are hydrogenated to the corresponding alcohol.

The nickel catalyst employed in the second hydrogenation zone comprises metallic nickel when initially charged and is preferably supported. It has been surprisingly found that the nickel catalyst efficiently absorbs organo-sulfur moieties but that it nevertheless continues to efficiently hydrogenate the aldehyde to the desired alcohol. Thus, the catalyst serves to desulfurize the product alcohol as well as to catalyze the desired hydrogenation. As a result of the absorbtion of the organo-sulfur compounds, the metallic nickel is gradually sulfided in situ in the reaction zone. While it is believed that at least part of the sulfided portion of the catalyst comprises nickel subsulfide ($Ni_3S_2$), the precise form of the catalyst after partial or complete in situ sulfurization is not known, due in part to the complex mixture of organo-sulfur compounds with which the catalyst comes into contact and the incomplete understanding into the mechanisms of absorbtion, desorbtion and reaction of these organo-sulfur compounds with the catalyst.

The nature of the nickel catalyst support is not critical to the hydrogenation and desulfurization achieved by the process of this invention. Thus, the nickel support can comprise kieselguhr, alumina, silica or other stable supports. However, it has been surprisingly found that alcohols having greatly improved properties are obtained when the nickel catalyst comprises a support having a low acidity and an initial surface area of from 20 to 120 $m^2$/gram. Exemplary of such preferred, low acidity supports are gamma-alumina, eta-alumina, silica and the like.

The relative amounts of the supported first stage sulfided and second stage Ni catalysts which are employed in the practice of this invention will depend on such factors as the degree of catalyst loading (the weight percent of the catalytically active metal sulfide or metal on the selected support) and other factors. Generally, for a supported $MoS_2$ catalyst containing from 10 to 15 wt. % $MoS_2$, and a supported Ni catalyst containing from about 30-60 wt. % Ni, the supported catalysts will be employed in the process of the present invention in a supported MoS$_2$:supported Ni catalyst volume:volume ratio of from about 0.2:1 to 10:1, and preferably of from about 0.3:1 to 9:1.

The aldehyde feed to the second hydrogenation zone is generally passed thereto at a liquid hourly space velocity of from about 0.2 to 1.0 v/v/hr., and more preferably from about 0.35 to 0.70 v/v/hr.

The temperature selected for use in the second hydrogenation zone should be less, preferably at least 5° C. less, and more preferably at least about 10° C. less, than the temperature selection for use in the first hydrogenation zone. To control the exothermic hydrogenation reaction to within the desired temperature ranges, the feed to the second hydrogenation zone can be cooled (e.g., to a temperature of from 10° to 50° C.) as necessary, e.g., by passing the first zone's effluent to an appropriate heat exchanger prior to the second hydrogenation. Alternatively, any hydrogen stream to be separately introduced to the second hydrogenation zone can be first cooled so that the exotherm in the second hydrogenation zone will not be sufficient to exceed the desired operating temperatures. Of course, temperature control in the second zone can be effected by use of a combination of such methods for interstage cooling of the aldehyde/alcohol effluent from the first hydrogenation zone and pre-cooling the hydrogen feed to the second zone.

The addition of 2 to 10 volume % water into the first and/or the second hydrogenation zones may be advantageously employed to help control hydrogenation temperature and to diminish the formation of by-products such as hydrocarbons, acetals, ethers and the like, during the hydrogenation step.

The effluent withdrawn from the second hydrogenation zone containing the desired alcohol product will generally also comprise unreacted aldehyde and high-boiling by-products formed in the oxo reactors and/or during hydrogenation, and will contain reduced amounts of organo-sulfur impurities (as compared to the sulfur content in the feed to the hydrogenation process of this invention). The precise composition of this effluent will vary widely, depending on such factors as the hydrogenation conditions of temperature and pressure, the hydrogenation feed composition, the liquid hourly space velocity in the hydrogenation zones and other factors. Generally, the effluent will comprise from about 70 to 99 wt.%, and preferably from about 80 to 95 wt.%, aliphatic alcohol product, from about 0.01 to 0.5 wt.%, and preferably from about 0.01 to 0.2 wt.%, unreacted aldehyde, from about 1 to 20 wt.%, and preferably from about 5 to 10 wt.%, high-boiling organic compounds, and less than about 40 ppm, preferably about 10 ppm, organo-sulfur impurities. The effluent from the second hydrogenation zone will also preferably have a carbonyl number of less than about 0.5, and more preferably less than about 0.3, mg KOH/gram of effluent sample.

The product alcohol can be recovered from the effluent withdrawn from the second hydrogenation zone by any conventional means, such as by a series of distillations: a first to remove lighter boiling compounds, followed by a separate distillation to recover the product alcohols as overhead and to form a bottoms product which can then be subjected to a further distillation to ensure removal of substantially all of the lighter boiling materials and alcohol as overhead and to form a second bottoms product comprising heavies. Preferably, the second hydrogenation zone's effluent is first degassed, using conventional methods and equipment, and is then contacted with an aqueous sodium hydroxide solution, again using conventional methods and equipment, to neutralize any acidic oxo or hydrogenation by-products prior to distillation of the effluent for recovery of the product alcohols.

If desired, the degassed effluent can be contacted, either before or after the above-described neutralization step, with a compound such as sodium borohydride which is useful for converting residual aldehyde content to alcohol. Such a borohydride treatment process is described in "Organic Chemistry", R. J. Morrison and R. N. Boyd, p. 636, 3d Ed. (1973).

It will be understood that conventional equipment can be used to effect the hydrogenation in the first and second hydrogenation zones in accordance with the process of this invention and that each hydrogenation zone can comprise a single reactor or a plurality of such reactors, arranged in series or parallel.

EXAMPLE 1

To illustrate the low degree of light-make which has been found to be achieved by use of a nickel on alumina catalyst in the second hydrogenation zone of this invention, a series of tests are performed in parallel train reactors. Each reactor train comprises a first 300 cc carbon steel reactor containing 200 cc of 10% by weight of molybdenum disulfide on carbon catalyst, and a second 75 cc carbon steel reactor containing 50 cc of either (A) 10% by weight molybdenum disulfide on carbon catalyst, (B) 52% by weight nickel on kieselguhr, or (C) 43 wt.% nickel on alumina. Catalyst "B" is produced by reducing a 7×1 14 mesh nickel and nickel oxide on kieselguhr catalyst (Girdler G49B, manufactured by United Catalyst Industries) in situ in the reactor by passing hydrogen gas (130 liters per hour, 3,000 psig) over the catalyst at a temperature of about 427° C. for 12 hours. Similarly, catalyst "C" is produced by reducing a nickel and nickel oxide on alumina catalyst (Girdler G87, manfactured by United Catalyst Industries) in situ in the reactor by passing gaseous hydrogen (130 liters per hour, 3000 psig) over this catalyst at a temperature of about 427° C. for 12 hours.

A liquid aldehyde feed comprising 24 wt.% decylaldehyde, 28 wt.% decyl alcohol, 27 wt.% didecylacetal of decylaldehyde, 14 wt.% unconverted C$_9$ olefin, 7 wt.% heavy materials (boiling higher than the other above components) and 15 ppm by weight of organo-sulfur compounds (calculated as elemental S) and having a carbonyl number of about 100 is passed at a rate of 150 cc/hour through the first reactor in each train at a temperature of about 234° C. The aldehyde is hydrogenated in the presence of hydrogen (3,000 psig), which is separately injected into each reactor at a rate of about 120 to 140 liters per hour, and also in the presence of water vapor which is introduced separately into each reactor at a rate of about 8 wt.%, based on the total aldehyde feed to the reactor. (All of the reactors in each train are heated by means of individually controlled fluidized sand baths.) The organo-sulfur compounds comprise a mixture of methyl propyl sulfide, methyl propyl sulfoxide and methylpropyl sulfone.

The partially hydrogenated liquid effluent from the first reactor in each train is analyzed and is found to have a carbonyl number of about 8.0 and to contain 15 ppm organo-sulfur compounds (calculated as S).

Each partially hydrogenated effluent is then passed to the second reactor in the appropriate reactor train, employing a feed rate for this liquid of about 150 cc per hour. In the second reactor the partially hydrogenated effluent is further hydrogenated at the selected temperature in the presence of gaseous hydrogen (3,000 psig) which is passed thereto at the rate of about 120 to 140 liters per hour, and also in the presence of water, which is introduced to each second reactor at about 8 wt.%, based on the partially hydrogenated feed to the second reactor.

The hydrogenated effluent from each second reactor is then analyzed by gas chromatography to determine the amount of lights make, that is, to determine the amount of materials boiling lower than the feed aldehyde or product alcohol (e.g., olefin and paraffins).

A series of runs is made in which the temperature of the second reactor is varied to determine, for each catalyst, the effect of temperature on the percent increase in lights make across the reactors. The data thereby obtained is set forth in Table I below.

These data indicate that, over the temperature range that is tested, the quantity of lights make across the second reactor is not significantly increased by the molybdenum disulfide/nickel-alumina catalyzed hydrogenation, as compared to the prior art method in which the hydrogenation catalyst consists of only molybdenum disulfide on carbon. In contrast, the molybdenum-disulfide/nickel-on-kieselguhr catalyst results in an increased lights make, at temperatures of greater than about 227°–230° C., which represents a significant and generally unacceptable yield loss.

TABLE I

| Temp[1] (°C.) | Percent (%) Increase in Lights Make[2] | | |
|---|---|---|---|
| | Catalyst A (MoS$_2$/C) | Catalyst B (Ni/Kieselguhr) | Catalyst C (Ni/Alumina) |
| 200 | — | 0 | 0 |
| 215 | — | 2 | 0 |
| 227 | — | 6 | 0 |
| 238 | — | 17 | 0 |
| 244 | 2 | — | — |
| 250 | — | 50 | 3 |
| 255 | 4 | — | — |
| 260 | 10 | 61 | 8 |

[1]Temperature of second reactor.
[2]Calculated by difference: (wt. % lights concentration in second reactor effluent minus wt. % lights concentration in aldehyde feed to the second reactor).

EXAMPLE 2

To illustrate the surprisingly superior quality of the alcohol which is produced employing a dual staged molybdenum-disulfide nickel-alumina catalyst system according to the process of this invention, the procedure of Example 1 is repeated, employing a temperature in the first reactor of 238° C. for each reactor train and a temperature of 238° C. for the second reactor for series (A) (the molybdenum sulfide-on-carbon second catalyst), and a temperature of 245° C. for both series B and C, i.e., for the nickel-on-kieselguhr and nickel-on-alumina catalyst reactors, respectively.

The alcohol-containing effluent from the second reactor in each train in then caustic treated to neutralize any acidic moieties formed during the hydrogenation and to avoid product degradation in subsequent processing of the alcohol. In each case, the respective alcohol effluent is contacted with 500 cc of a 1.6 wt.% sodium hydroxide aqueous solution and is stirred at a temperature of 150° C. for a period of 2 hours. At the end of this time, stirring is ceased and the liquid is allowed to settle, thereby forming an organic and aqueous phase. The organic phase is recovered and washed with fresh water at a temperature of 150° C. with mixing for a period of 0.5 hour. This washed liquid is then allowed to settle and an organic phase results which comprises the washed alcohol product. A 3 liter sample of each washed alcohol is then distilled using a 25 mm diameter glass Podbielniak distillation column using the following procedure: the liquid is brought to reflux temperature at a pressure of 100 mm Hg. Liquid takeoff from the overhead condenser is begun at a 10:1 reflux ratio which is maintained until the overhead is water free. Then, cut No. 1 is obtained after changing to a 20:1 reflux ratio and proceeding to a 93.3° C. vapor (overhead) temperature. Cut No. 2 is taken after changing to a 50:1 reflux ratio and proceeding to a 132.2° C. vapor (overhead) temperature. Cut No. 3 is then taken at the 50:1 reflux ratio at temperatures within the range of greater than 132.2° C., up to 143.3° C. At 143.3° C., the reflux ratio is changed to 5:1 and Cut No. 4 is taken until the liquid (still pot) temperature reaches 232.2° C. (regardless of vapor temperature). Cut No. 4 is the product alcohol that is recovered and used in the following study.

To each caustic treated and distilled alcohol sample (approximately 3 liters) is then added 0.5 gm of sodium borohydride, and the resulting mixture is stirred for 6 hours to insure complete dissolution of the sodium borohydride. Thereafter, each sample is filtered through Decalite (speed plus) diatomaceous earth and is then employed as follows to prepare phthalate esters.

In a first run in each series, a 655 gram sample of the selected alcohol is reacted with 245 grams of phthalic anhydride employing 0.0165 gram of para-toluene sulfonic acid as catalyst. Thus, the alcohol is employed in a 25 wt.% excess. The esterification reaction is effected with stirring at a temperature of 160° C. until 99% conversion of the phthalic anhydride is reached (about 2 hours). Thereafter, the crude esters are neutralized with 8 grams of solid sodium carbonate which is added to the crude esters with mixing, and the neutralized esters are quenched by 131 cc of water. Thereafter, the quenched, neutralized ester solution is washed repeatedly with 130 cc of water. The resulting washed ester is steam stripped to remove excess alcohol, which is collected as distillate. The stripped phthalate ester is then contacted with carbon and clay in a flask open to the atmosphere and heated by means of a heating mantle, at a temperature of 90° C. for one hour to decolor the ester. Thereafter, the ester is filtered using Decalite (speed plus) diatomaceous earth. The color of each thus-obtained finished ester is determined.

The excess alcohol recovered from each steam stripping is then employed as feed to a second such esterification and the resulting crude esters prepared from this recycle alcohol are finished as described above and the color of each finished ester is determined. In a third run in each series, recycle alcohol collected as distillate during steam stripping in the second run is employed as feed to yet a third such esterification and the crude esters are treated as described above to give finished esters.

The data thereby obtained are set forth in Table II below. Organo-sulfur levels are reported on an elemental sulfur basis.

TABLE II

| Series | Catalyst | Run | Carbonyl No.[1] | Hydroxyl No.[2] | Feed Alcohol ppm S[3] | Crude Ester ppm S[3] | Pt/Co Crude Ester[4] | Pt/Co Color No. Finished Ester[4] |
|---|---|---|---|---|---|---|---|---|
| A | (MoS$_2$ on carbon) | 1 | .05 | 348 | 7 | 164 | 50 | 35 |
|   |   | 2 | .25 | 337 | 25 | — | 25 | 30 |
|   |   | 3 | .32 | 321 | 50 | <10 | — | 200 |
| B | (MoS$_2$ + Ni on Kieselguhr) | 1 | .03 | 347 | 9 | 5.5 | 50 | 35 |
|   |   | 2 | .48 | 334 | 15 | 197 | 25 | 15 |
|   |   | 3 | .41 | 307 | 85 | — | — | 300 |
| C | (MoS$_2$ + Ni on alumina) | 1 | .05 | 349 | 7 | 5.5 | 10 | 15 |
|   |   | 2 | .14 | 334 | 9 | 151 | 35 | 25 |
|   |   | 3 | .20 | 306 | 75 | — | — | 35 |

[1]Per method discussed in S. A. Bartkiewicz and L. C. Kenyon, "Automated Determination of Trace Carbonyls", Analytical Chemistry, Vol. 35, no. 3, pp. 1122-1123 (March 1963).
[2]Mg.KOH/gm alcohol sample.
[3]Sulfur analysis for S < 10 ppm - sulfur analyzer (Model S300), Houston-Atlas; for S ≧ 10 ppm - Dohrmann (Model S300) Pyrolysis Furnace.
[4]ASTM Method No. D1209.

EXAMPLE 3

In order to compare the performance of different Ni catalysts in the process of this invention over extended times of operation, the nickel on alumina catalyst (Catalyst "C") and nickel on kieselguhr catalyst (Catalyst "B") prepared as in Example 1, are employed in a hydrogenation using the second reactor aldehyde feed and procedure employed in Example 1 over prolonged periods. Each catalyst is tested before the test and after its removal from the reactor to determine its surface area, pore volume, carbon content and sulfur content. The data thereby obtained are set forth in Table III below.

As these data indicate, the aged Ni/alumina catalyst absorbed sulfur and retained its surface area, whereas the Ni/kieselguhr catalyst's surface area was decreased over 40% during this time. Since hydrogenation activity of these catalysts decreases as surface area is decreased, it can be seen that the activity of the Ni/alumina catalyst (Catalyst "C") was not adversely affected by any decreased surface area. Also, the data show that the pore volume of the Ni/alumina catalyst is slightly increased during the test, whereas the Ni/kieselguhr suffered a decline in pore volume.

The Ni/alumina's carbon content after 4413 hours is found to be much less than that determined after only 4137 hours for the kieselguhr-supported catalyst. Since pore mouth plugging can result from excessive carbon deposits, the decreased porosity of Catalyst B can be at least partially attributed to the higher rate of carbon deposits on the latter catalyst.

TABLE III

| Catalyst | C | C | B | B |
|---|---|---|---|---|
| Age, hours | 0 | 4413 | 0 | 4137 |
| Surface area, sq. meters/gm.[1] | 43 | 43 | 164 | 96 |
| Pore volume, cc/gm[2] | 0.27 | 0.30 | 0.19 | 0.17 |
| Carbon content, wt %[3] | ~0 | 2.37 | ~0 | 7.09 |
| Sulfur content, wt %[4] | ~0 | 1.83 | ~0 | 2.25 |
| Bulk density, gm/cc | 0.83 | N.D. | 1.12 | N.D. |

[1]Determined by BET N$_2$ absorption
[2]Determined by N$_2$ absorption
[3]Determined by combustion of catalyst in air at 1000° C. and measuring volume of CO$_2$ gas given off
[4]X-ray analysis
[5]Determined from volume and weight measurements
N.D. = not determined

EXAMPLE 4

A series of runs are made to compare the performance of the aged Catalyst C, which is obtained at the conclusion of the 4,413-hour run in Example 3, and a pre-sulfided nickel catalyst (Catalyst "D").

Catalyst D comprises Ni$_3$S$_2$ on alumina and is prepared by contacting 50 cc of nickel and nickel oxide on alumina catalyst (Gridler G87, manufactured by United Catalyst Industries) in a heated quartz tube with a hydrogen gas containing 15 volume percent hydrogen sulfide (space velocity of 1,000 v/v/hr.) at a temperature of 316° C. and atmospheric pressure for a period of six hours.

Fifty cc of each of the above catalysts are charged to separate 75 cc carbon steel reactors and are then contacted, at a temperature of 232° C. and at 3,000 psig pressure, with a liquid aldehyde feed (liquid feed rate=150 cc/hr.) comprising 46.1 wt.% decyl aldehyde, 11.9 wt.% decyl alcohol, 10.6 wt.% didecylacetal of decylaldehyde, 20.9 wt.% unconverted C$_9$ olefin, 3.4 wt.% heavy materials and 15 ppm by weight of organosulfur compounds (calculated as elemental S) and having a carbonyl number of about 163. Gaseous hydrogen is also separately injected into each reactor at a rate of about 120-140 liters per hour, and water vapor is also separately introduced into each reactor at a rate of about 12 cc per hour.

At the end of 168 hours of operation, the effluent from each reactor is analyzed to determine the lights make across each reactor, the reaction rate constant (for conversion of the aldehyde to corresponding alcohol) and the quantity of by-product acid made across the reactor. The data thereby obtained are set forth in Table IV below.

TABLE IV

| Catalyst | % Increase in Lights Make[2] | Hydrogenation Reaction Rate Constant[3] k (hr$^{-1}$) | Acid No.[4] |
|---|---|---|---|
| Aged Ni/Alumina[1] | 0 | 4.8 | 3.0 |

TABLE IV-continued

| Catalyst | % Increase in Lights Make[2] | Hydrogenation Reaction Rate Constant:[3] k (hr$^{-1}$) | Acid No.[4] |
|---|---|---|---|
| Ni$_3$S$_2$/alumina | 7.6 | 3.5 | 11.8 |

[1] Aged 4413 hours as in Example 3.
[2] Calculated by difference (weight percent concentration of lights in reactor effluent minus weight percent concentration of lights in aldehyde feed to the reactor).
[3] Determined after 168 hours.
[4] Mg KOH/mg sample determined by KOH titration of aldehyde feed and reactor effluent samples (acid number of aldehyde feed = 3.6).

Therefore, it can be seen that the nickel/alumina catalyst (Catalyst C) which is exposed in situ to organo-sulfur compounds in the aldehyde feed of Example 3 for 4,413 hours, provides unexpectedly superior performance to a pre-sulfided catalyst comprising nickel subsulfide (Ni$_3$S$_3$). In particular, the aged Catalyst C does not provide any increase in the lights make across the reactor, whereas the nickel subsulfide catalyst provided an increase of 7.6 percent, i.e., increases the light concentration from 20.9 wt.% in the feed to a concentration of 27.6 wt.% in the liquid reactor effluent. Furthermore, the aged nickel catalyst is significantly more active for hydrogenation of the aldehyde, thereby permitting significantly improved efficiencies of hydrogenation for a given catalyst bed size or, alternatively, permitting the use of a smaller bed size for a given degree of aldehyde conversion. Finally, whereas the aged nickel/alumina catalyst provides a decrease in the acid moieties across the reactor, the nickel subsulfide catalyst effects an acid number increase of approximately three times as a result of an increased amount of acids formed in the reactor over this presulfided catalyst.

It will be obvious that various changes and modifications may be made without departing from the invention and it is intended, therefore, that all matter contained in the foregoing description shall be interpreted as illustrative only and not limitative of the invention.

What is claimed is:

1. An improved process for hydrogenating oxo aldehydes to the corresponding oxo alcohols in the presence of organo-sulfur impurities which comprises:

(a) contacting an aldehyde feed containing organo-sulfur compound impurities in a first reaction zone at a temperature within the range of from about 180° to 260° C. in the presence of a sulfided hydrogenation catalyst and in the presence of gaseous hydrogen to hydrogenate at least a portion of said aldehydes to said alcohols, thereby forming a partially hydrogenated effluent consisting of organo-sulfur compound impurities, product alcohol and unreacted aldehyde; and (b) directly introducing said partially hydrogenated effluent, after optionally performing one or more of the steps of (i) cooling said effluent and (ii) degassing said effluent to remove excess hydrogen, to a second hydrogenation zone wherein at least a portion of the unreacted aldehydes are hydrogenated in the presence of a metallic nickel catalyst comprising nickel on alumina and in the presence of from about 175° to 250° C., said temperature in said second hydrogenation zone being lower than the temperature employed in said first hydrogenation zone.

2. The process according to claim 1 wherein said aldehyde comprises a saturated aliphatic aldehyde having from 6 to 20 carbon atoms.

3. The process according to claim 1 wherein said aldehyde feed to the first hydrogenation zone comprises from about 10 to 90 wt.% saturated aliphatic aldehyde having from 6 to carbon atoms, and from about 5 to 60 wt. % of saturated aliphatic alcohols having from 6 to 18 carbon atoms, and further contains organo sulfur impurities in an amount of from about 5 to 500 ppm, calculated as elemental sulfur.

4. The process according to claim 1 wherein said first hydrogenation catalyst comprises molybdenum disulfide on carbon, and wherein said aldehyde feed is introduced to the first hydrogenation zone at a liquid hourly space velocity of from about 0.3 to 2 v/v/hr., and said effluent introduced to said second hydrogenation zone is thus introduced at a liquid hourly space velocity of from about 0.2 to 1 v/v/hr.

5. The process according to claim 4 wherein the liquid feed to each hydrogenation zone additionally comprises from about 2 to 10 volume percent water.

6. The process according to claim 4 wherein the temperature of said second hydrogenation zone is at least 5° C. lower than the temperature employed in said first hydrogenation zone, and wherein said molybdenum sulfide catalyst is employed in an amount of from about 0.2 to 10 per part by volume of said nickel catalyst.

7. The process according to claim 1 wherein said organo-sulfur impurities are selected from the group consisting of sulfides, sulfones and sulfoxides.

8. The process of claim 1 wherein the sulfided hydrogenation catalyst is selected from the group consisting of sulfides of molybdenum, tungsten and nickel, and mixtures thereof.

* * * * *